(12) United States Patent
Hannen et al.

(10) Patent No.: US 8,445,720 B2
(45) Date of Patent: *May 21, 2013

(54) UNSATURATED DICARBOXYLIC ACIDS FROM UNSATURATED CYCLIC HYDROCARBONS AND ACRYLIC ACID BY WAY OF METATHESIS, THE USE THEREOF AS MONOMERS FOR POLYAMIDES, POLYESTERS AND POLYURETHANES, AND SUBSEQUENT REACTION TO DIOLS AND DIAMINES

(75) Inventors: Peter Hannen, Recklinghausen (DE); Martin Roos, Haltern am See (DE); Harald Haeger, Luedinghausen (DE)

(73) Assignee: Evonik Degussa GmbH, Essen (DE)

( * ) Notice: Subject to any disclaimer, the term of this patent is extended or adjusted under 35 U.S.C. 154(b) by 290 days.

This patent is subject to a terminal disclaimer.

(21) Appl. No.: 12/865,018

(22) PCT Filed: Apr. 17, 2009

(86) PCT No.: PCT/EP2009/054599
§ 371 (c)(1),
(2), (4) Date: Jul. 28, 2010

(87) PCT Pub. No.: WO2009/144094
PCT Pub. Date: Dec. 3, 2009

(65) Prior Publication Data
US 2010/0312012 A1 Dec. 9, 2010

(30) Foreign Application Priority Data

May 30, 2008 (DE) .......................... 10 2008 002 090

(51) Int. Cl.
*C07C 57/13* (2006.01)
(52) U.S. Cl.
USPC ........................................................ 562/595
(58) Field of Classification Search
None
See application file for complete search history.

(56) References Cited

U.S. PATENT DOCUMENTS

| | | | |
|---|---|---|---|
| 2,960,533 A * | 11/1960 | Frank et al. | 562/593 |
| 6,828,449 B2 | 12/2004 | Herwig et al. | |
| 6,861,540 B2 | 3/2005 | Herwig et al. | |
| 6,927,308 B2 | 8/2005 | Leininger et al. | |
| 7,084,300 B2 | 8/2006 | Herwig et al. | |
| 7,253,329 B2 | 8/2007 | Herwig et al. | |
| 7,495,129 B2 | 2/2009 | Balduf et al. | |
| 7,608,738 B2 | 10/2009 | Herwig et al. | |
| 2002/0198426 A1 | 12/2002 | Morgan et al. | |
| 2007/0004903 A1 | 1/2007 | Hoff et al. | |
| 2007/0265184 A1 | 11/2007 | Herwig et al. | |
| 2009/0306367 A1 | 12/2009 | Roos et al. | |

FOREIGN PATENT DOCUMENTS
WO 02 079127 10/2002

OTHER PUBLICATIONS

Saito, I. et al., "Synthesis of α, ω-Dicarboxylic Acids and Unsaturated Carboxylic Acids From Silyl Enol Ethers", Tetrahedron Letters, vol. 24, No. 41, pp. 4439-4442 (Jan. 1, 1983) XP-002529873.
English, Jr. J., "The Wound Hormones of Plants. V. The Synthesis of Some Analogs of Traumatic Acid", Journal of the American Chemical Society, vol. 63, pp. 941-943 (Apr. 1941) XP-002551611.
International Search Report issued Nov. 4, 2009 in PCT/EP09/54599 filed Apr. 17, 2009.
U.S. Appl. No. 13/142,505, filed Jun. 28, 2011, Meier, et al.
U.S. Appl. No. 13/424,548, filed Mar. 20, 2012, Hannen, et al.
U.S. Appl. No. 13/806,555, filed Dec. 21, 2012, Hannen, et al.

* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

The invention relates to a method for producing α,β-unsaturated dicarboxylic acids and the corresponding saturated dicarboxylic acids, whereby the corresponding cycloalkene and acrylic acid are reacted with a ruthenium catalyst by way of a metathesis reaction at high substrate concentrations until the reaction takes place in substance, the resulting dicarboxylic acid being precipitated.

11 Claims, No Drawings

UNSATURATED DICARBOXYLIC ACIDS FROM UNSATURATED CYCLIC HYDROCARBONS AND ACRYLIC ACID BY WAY OF METATHESIS, THE USE THEREOF AS MONOMERS FOR POLYAMIDES, POLYESTERS AND POLYURETHANES, AND SUBSEQUENT REACTION TO DIOLS AND DIAMINES

α,β-Unsaturated dicarboxylic acids can be prepared from cyclic hydrocarbons such as cyclooctadiene (COD), cyclododecene (CDEN), cyclododecatriene (CDT), cycloheptene, cyclohexene and cyclopentene by means of a metathesis reaction using a suitable catalyst (Scheme 1).

Scheme 1: General reaction for preparing unsaturated dicarboxylic acids (2) from cyclic unsaturated hydrocarbons (1) by metathesis with acrylic acid.

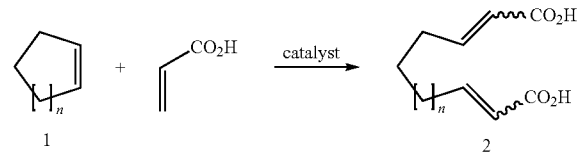

Polyamides or polyesters can be obtained from the resulting α,β-unsaturated dicarboxylic acids by polycondensation with diamines or diols. A particular feature of these plastics is the possibility of crosslinking via the double bonds. The corresponding saturated dicarboxylic acids can be obtained in one step by hydrogenation. Furthermore, these compounds can be converted without a great outlay into the corresponding diols and diamines. Apart from polyesters, the diols can also be used for preparing polyurethanes.

PRIOR ART

The process described here represents a considerable improvement on conventional processes.
(Morgan, John, P., Morrill, Christie; Grubbs, Robert, H.; Choi, Tae-Lim WO 02/079127A1.
Choi, T-L.; Lee, C. W.; Chatterjee, A. K.; Grubbs, R. H. J. Am. Chem. Soc. 2001, 123, 10417-10418.
Randl, S.; Connon, S. J.; Blechert, S. J. Chem. Soc., Chem. Commun. 2001, 1796-1797.)

Hitherto, the above-described reaction had to be carried out in high dilution in order to suppress oligomerization or polymerization as competitive reaction. In addition, dichloromethane is predominantly used as solvent, which is disadvantageous for an industrial reaction because of its health hazard potential.

It has now surprisingly been found that a process according to the claims makes it possible to shift the equilibrium completely in the direction of the desired product without having to work in high dilution. In addition, the process described makes effective recycling of the catalyst possible. This is achieved by, in contrast to previous practice, working at high substrate concentrations up to reactions in bulk. During the reaction, the α,β-unsaturated dicarboxylic acid precipitates when the solubility product is exceeded and is thus withdrawn from the equilibrium (in the homogeneous phase).

A decisive advantage of the invention described here is thus the fact that the product precipitates as solid during the reaction. Since ring-opening cross-metathesis is an equilibrium reaction, there is the possibility, in addition to the liberation of ethylene, to shift the equilibrium to the side of the desired product. Even when the conversion is not complete at a point in time x or part of the product remains in solution, complete conversion of starting material can ultimately be achieved in a continuous mode of operation.

Apart from the effective influencing of the reaction equilibrium in favor of the product, the ease of separating off the products and, associated therewith, recovering the catalyst makes carrying out the process much easier. The catalyst used remains in solution and can be recycled.

In previous processes, the reaction mixture has to be worked up as a whole. This is effected by distilling off the solvent and purifying the residue by chromatography. The chromatographic purification of the crude product, in particular, requires the use of large amounts of solvent and energy to remove the latter, which is impractical for an industrial reaction.

The reaction described is carried out at temperatures of from 10 to 100° C., preferably from 20 to 80° C. and particularly preferably from 20 to 60° C.

The reaction described can be carried out both in bulk and using a solvent. Suitable solvents are acyclic and cyclic hydrocarbons. Aromatic halogenated hydrocarbons are particularly suitable and aromatics bearing alkyl groups are very particularly suitable.

When the reaction is carried out in solution, cycloalkene concentrations of >1 M are preferred. Particular preference is given to concentrations of from 1 to 2 M and very particular preference is given to cycloalkene concentrations of from 2 to 4 M, based on the solvent.

In the process described, the catalyst is used in amounts of from 5 to 0.0001 mol %, based on the amount of unsaturated cycloalkene. Preference is given to amounts of from 2 to 0.001 mol % and particular preference is given to from 1 to 0.5 mol % of catalyst, based on the molar amount of unsaturated cycloalkene used.

To obtain the α,β-unsaturated dicarboxylic acid in polymer grade quality, purification by means of crystallization, distillation or a combination of the two is possible.

Suitable catalysts are ruthenium-carbene complexes which, as one of the characteristic features, bear an N-heterocyclic carbene ligand. Examples of preferred catalysts are shown in FIG. 1. Particular preference is here given to catalysts of type 7 having an electron-pulling group R' on the benzylidene ligand.

Figure 1: Examples of ruthenium catalysts used

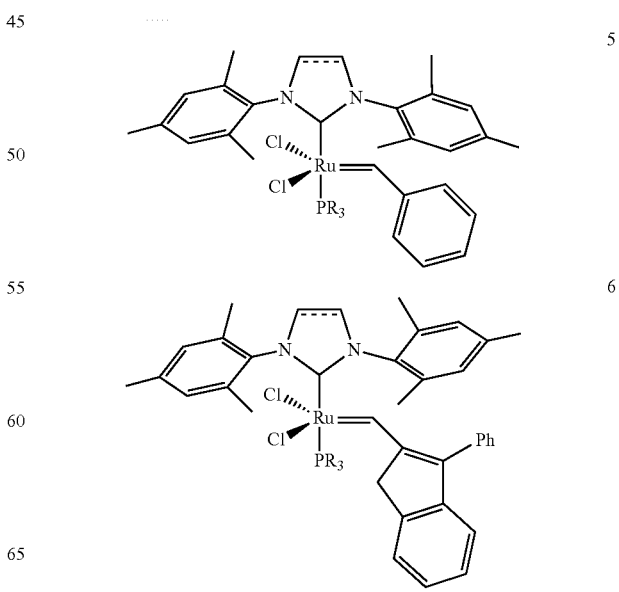

-continued

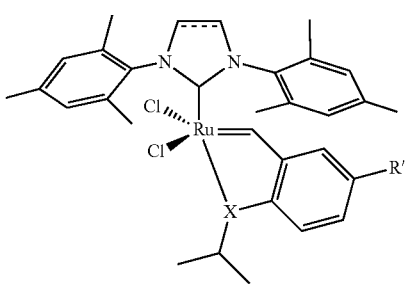

EXAMPLES 1. 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (1 mol % based on the cycloalkene) is placed together with toluene (2.25 ml) under argon in a Schlenk vessel. A solution of cyclopentene (0.3 g, 4.4 mmol) and acrylic acid (0.79 g, 11 mmol) in toluene (2.25 ml) is added dropwise to the catalyst solution. The reaction mixture is stirred at 60° C. for one hour and subsequently cooled to room temperature. The solid which precipitates is filtered off, washed with a little cold toluene and dried under reduced pressure. The product was obtained as a white solid (0.128 g, 16%). A purity of 98.9% was determined by NMR analysis.

2. 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (1 mol % based on the cycloalkene) is placed together with toluene (1.75 ml) under argon in a Schlenk vessel. A solution of cyclohexene (0.3 g, 3.65 mmol) and acrylic acid (0.66 g, 9.13 mmol) in toluene (1.75 ml) is added dropwise to the catalyst solution. The reaction mixture is stirred for one hour at 60° C. and subsequently cooled to room temperature. The solid which precipitates is filtered off, washed with a little cold toluene and dried under reduced pressure. The product was obtained as a white solid (0.272 g, 38%). A purity of 99.2% was determined by NMR analysis.

3. 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (1 mol % based on the cycloalkene) is placed together with toluene (1.50 ml) under argon in a Schlenk vessel. A solution of cycloheptene (0.3 g, 3.12 mmol) and acrylic acid (0.56 g, 7.80 mmol) in toluene (1.50 ml) is added dropwise to the catalyst solution. The reaction mixture is stirred for one hour at 60° C. and subsequently cooled to room temperature. The solid which precipitates is filtered off, washed with a little cold toluene and dried under reduced pressure. The product was obtained as a white solid (0.223 g, 14%). A purity of 91% was determined by NMR analysis.

4. 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (1 mol % based on the cycloalkene) is placed together with toluene (1.80 ml) under argon in a Schlenk vessel. A solution of cyclooctadiene (0.4 g, 3.70 mmol) and acrylic acid (1.33 g, 18.49 mmol) in toluene (1.80 ml) is added dropwise to the catalyst solution. The reaction mixture is stirred for one hour at 60° C. and subsequently cooled to room temperature. The solid which precipitates is filtered off, washed with a little cold toluene and dried under reduced pressure. The product was obtained as a white solid (0.158 g, 25%). A purity of 98% was determined by HPLC analysis.

5. 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride (1 mol % based on the cycloalkene) is placed together with toluene (1.50 ml) under argon in a Schlenk vessel. A solution of cycloheptene (0.3 g, 3.12 mmol) and acrylic acid (0.56 g, 7.80 mmol) in toluene (1.50 ml) is added dropwise to the catalyst solution. The reaction mixture is stirred at 60° C. for one hour and subsequently cooled to room temperature. The solid which precipitates is filtered off, washed with a little cold toluene and dried under reduced pressure. The product was obtained as a white solid (0.223 g, 14%). A purity of 91% was determined by NMR analysis.

The invention claimed is:

1. A process for preparing unsaturated dicarboxylic acids, comprising
    metathesis reacting
    unsaturated cyclic hydrocarbons and acrylic acid wherein
        the reaction is carried out in solution and the unsaturated cyclic hydrocarbon is present in concentrations of >1 mol/l in the presence of a ruthenium catalyst to produce dicarboxylic acid, and precipitating the dicarboxylic acid from the said reaction,
    wherein said unsaturated cyclic hydrocarbon is at least one selected from the group consisting of cyclooctadiene, cyclododecene, cyclododecatriene and cycloheptene and
    wherein a solvent for said reaction is not dichloromethane.

2. The process as claimed in claim 1,
    wherein
    the reaction is carried out in solution and the unsaturated cyclic hydrocarbon is present in concentrations of from 2 to 4 mol/l.

3. The process as claimed in claim 1,
    wherein the ruthenium catalyst is a
    ruthenium-carbene complex which comprises an N-heterocyclic ligand.

4. The process as claimed in claim 1,
    wherein
    the ruthenium catalyst is present in an amount of from 5 to 0.0001 mol %, based on the molar amount of unsaturated cyclic hydrocarbon.

5. The process as claimed in claim 1,
    wherein
    the ruthenium catalyst is present in an amount of from 2 to 0.001 mol %, based on the molar amount of unsaturated cyclic hydrocarbon.

6. The process as claimed in claim 1,
    wherein
    the ruthenium catalyst is present in an amount of from 1 to 0.5 mol %, based on the molar amount of unsaturated cyclic hydrocarbon.

7. The process as claimed in claim 1
    comprising an
    acyclic or cyclic hydrocarbon solvent.

8. The process as claimed in claim 1,
    comprising an
    aromatic halogenated hydrocarbon solvent.

9. The process as claimed in claim 1,
    further comprising hydrogenating
    the dicarboxylic acid.

10. The process as claimed in claim 1,
    further comprising recycling
    the ruthenium catalyst dissolved in a filtrate.

11. The process as claimed in claim 1,
    further comprising purifying
    the unsaturated dicarboxylic acid by crystallization, distillation or a combination of the two.

* * * * *